US012358945B2

(12) United States Patent
Goklen et al.

(10) Patent No.: US 12,358,945 B2
(45) Date of Patent: *Jul. 15, 2025

(54) METHODS FOR PURIFYING ANTIBODIES (71) Applicant: GLAXOSMITHKLINE INTELLECTUAL PROPERTY (NO. 2) LIMITED, Stevenage (GB)

(72) Inventors: Kent E. Goklen, King of Prussia, PA (US); Eric J. Suda, Holly Springs, NC (US); Antonio Raul Ubiera, King of Prussia, PA (US)

(73) Assignee: GlaxoSmithKline Intellectual Property (No. 2) Limited, Stevenage (GB)

( * ) Notice: Subject to any disclaimer, the term of this patent is extended or adjusted under 35 U.S.C. 154(b) by 1338 days.

This patent is subject to a terminal disclaimer.

(21) Appl. No.: 15/931,062

(22) Filed: May 13, 2020

(65) Prior Publication Data

US 2020/0277330 A1    Sep. 3, 2020

Related U.S. Application Data

(63) Continuation of application No. 14/775,868, filed as application No. PCT/IB2014/059755 on Mar. 13, 2014, now Pat. No. 10,676,503.

(60) Provisional application No. 61/787,309, filed on Mar. 15, 2013.

(51) Int. Cl.
| | |
|---|---|
| *A61K 39/395* | (2006.01) |
| *B01D 15/38* | (2006.01) |
| *C07K 1/22* | (2006.01) |
| *C07K 16/06* | (2006.01) |

(52) U.S. Cl.
CPC ............ *C07K 1/22* (2013.01); *B01D 15/3809* (2013.01); *C07K 16/065* (2013.01); *C07K 2317/569* (2013.01)

(58) Field of Classification Search
None
See application file for complete search history.

(56) References Cited

U.S. PATENT DOCUMENTS

| | | | |
|---|---|---|---|
| 5,429,746 A | 7/1995 | Shadle et al. | |
| 10,259,842 B2 * | 4/2019 | Gruber | C11D 7/10 |
| 10,676,503 B2 * | 6/2020 | Goklen | C07K 16/065 |
| 2003/0152966 A1 | 8/2003 | Alred et al. | |
| 2008/0167450 A1 | 7/2008 | Pan | |
| 2008/0182979 A1 | 7/2008 | Lihme et al. | |
| 2016/0108084 A1 | 4/2016 | Gruber et al. | |

FOREIGN PATENT DOCUMENTS

| | | |
|---|---|---|
| CN | 1922207 A | 2/2007 |
| WO | WO/03102208 A2 | 12/2003 |
| WO | WO 2005/082937 | 9/2005 |
| WO | WO 2005/113604 A2 | 12/2005 |
| WO | WO 2007/109163 A2 | 9/2007 |
| WO | 2008031020 A2 | 3/2008 |
| WO | WO 2012/135415 A1 | 10/2012 |
| WO | 2014141150 A1 | 9/2014 |
| WO | 2014186350 A1 | 11/2014 |
| WO | 2015038888 A1 | 3/2015 |

OTHER PUBLICATIONS

Aboulaich et al., "A Novel Approach to Monitor Clearance of Host Cell Proteins Associated with Monoclonal Antibodies", Biotechnology Progress, vol. 30, No. 5, pp. 1114-1124 (2014).
Chollangi, S. et al., "Development of Robust Antibody Purification by Optimizing Protein-A Chromatography in Combination With Precipitated Methodologies", Biotechnology and Bioengineering (2015), vol. 112, No. 11, pp. 2292-2304.
Levy et al., "Development and characterization of a protein A capture step for improved impurity clearance", Process Development, Biopharmaceutical Development, King of Prussia, PA, Washes—ACS Biot Poster, Denver, 2015, 1 page.
Li, Heping, "The Production Principle and Technology of Fine Chemicals", Henan Science and Technology Press, p. 336, Sep. 30, 1994, 4 pages (C1).
"Clinical Medical Examination", Fuzhou Army General Hospital, Shanghai Science and Technology Press, p. 253, Apr. 30, 1978, 7 pages (C2).
Brodsky et al., "Caprylic acid precipitation method for impurity reduction: an alternative to conventional chromatography for monoclonal antibody purification", *Biotechnology and Bioengineering,* vol. 109, No. 10, pp. 2589-2598 (2012).
Chhatre, et al., "Evaluation of a novel agarose-based synthetic ligand adsorbent for the recovery of antibodies from ovine serum", *Journal of Chromatography B,* vol. 860, pp. 209-217 (2007).
Monie, Elin, "Evaluation of the 96-well format for screening of chromatographic buffer conditions", Master's degree project, pp. 1-55 (2006).
Newcombe et al., "Optimised affinity purificaiton of polyclonal antibodies from hyper immunised ovine serum using a synthetic Protein A adsorbent, MAbsorbent A2P", *J. of Chromatography B,* vol. 814, pp. 209-215 (2005).
Nilson et al., "Purification of antibodies using protein L-binding framework structures in the light chain variable domain", *Journal of Immunological Methods,* vol. 164, No. 1, pp. 33-40 (1993).

(Continued)

*Primary Examiner* — Yunsoo Kim
(74) *Attorney, Agent, or Firm* — Kelly A. Gauger (57) ABSTRACT

A method for purifying a protein comprising an antibody, antibody fragment, or immunoglobulin single variable domain, from a solution containing at least one contaminant by superantigen chromatography comprising: a) adsorbing the protein to the superantigen immobilized on a solid support; b) removing the at least one contaminant by contacting the immobilized superantigen containing the adsorbed protein with a first wash buffer comprising an aliphatic carboxylate; and c) eluting the protein from the superantigen immobilized on the solid support.

20 Claims, 3 Drawing Sheets

(56) References Cited

OTHER PUBLICATIONS

Tong et al., "Caprylate as the albumin-selective modifier to improve IgG purification with hydrophobic charge-induction chromatography", *Journal of Chromatography A*, vol. 1285, pp. 88-96 (2013).
Naik et al., "Performance of Hexamer Peptide Ligands for Affinity Purification of Immunoglobulin G from Commercial Cell Culture Media," Journal of Chromatography A, vol. 1218, (2011), pp. 1691-1700.
Anonymous: "Albumin in Cell Culture," Sigma-Aldrich, Oct. 26, 2008, pp. 1-2, XP055751730.
Chhatre S., et al., "Purification of Antibodies Using the Synthetic Affinity Ligand Absorbent MAbsorbent A2P," Nature Protocols, 2007, vol. 2(7), pp. 1763-1769.
Fraser J.D., et al., "The Bacterial Superantigen and Superantigen-like Proteins," Immunological Reviews, Oct. 2008, vol. 225, pp. 226-243.
Haiou Y., et al., "Purification of Human Immunoglobulin G via Fc-specific Small Peptide Ligand Affinity Chromatography," Journal of chromatography, Feb. 2009, vol. 1216(6), pp. 910-918.
Henry K.A., et al., "A Rational Engineering Strategy for Designing Protein a-binding Camelid Single-domain Antibodies," PLos One, Sep. 2016, vol. 11(9), pp. 1-18.
Le Merdy S., "Selection of Clarification Methods for Improved Downstream Performance and Economics," Bioprocessing Journal, Oct. 2015, vol. 14(3), pp. 50-55.
Liu Z., et al., "Effects of Peptide Density and Elution pH on Affinity Chromatographic Purification of Human Immunoglobulins A and M," Journal of Chromatography A, Nov. 2011, vol. 1218(46), pp. 8344-8352.

* cited by examiner

Figure 1 Caprylate Concentration Study Results – anti-OSM

Figure 2 Caprylate Concentration Study Results – anti-IL13

Figure 3 Carboxylic Acid Comparison Study Results

METHODS FOR PURIFYING ANTIBODIES

CROSS-REFERENCE TO RELATED APPLICATIONS

This application is a continuation of U.S. application Ser. No. 14/775,868, filed Sep. 14, 2015, which is a 371 of International Application No. PCT/IB2014/059755, filed Mar. 13, 2014, which claims the benefit of U.S. Provisional Application No. 61/787,309, filed Mar. 15, 2013, which are incorporated herein in their entirety.

FIELD OF THE INVENTION

The present invention relates to the field of protein purification using a superantigen such as Protein A, Protein G, or Protein L immobilized to a solid support. In particular, the invention relates to wash buffer components and method of using the wash buffers to remove host cell contaminants during wash steps, minimizing loss of the desired protein product.

BACKGROUND OF THE INVENTION

Over the past decade, protein A affinity chromatography has become well established as the primary method of choice for the capture of monoclonal antibodies (mAbs) from mammalian cell culture feed streams. This highly specific affinity step is able to remove 98% of impurities in a single step due to the specific binding between the protein A ligand and the Fc-region of the antibody. Under typical operating conditions in protein A chromatography, clarified cell culture feed streams are applied to the column until a certain load mass of antibody is achieved. The column is then typically washed with a high ionic strength buffer to remove host cell contaminants bound to the resin through nonspecific interactions. The antibody is then normally eluted from the column by a shift in pH and collected for further processing. The primary objective of this work is therefore to investigate the use of detergents combined with salts to disrupt both ionic and hydrophobic interactions and enhance removal of host cell contaminants, thereby reducing the purification burden on downstream unit operations.

For large-scale purification much effort is placed on optimizing the components of wash and elution buffers to maximize product yield. However, in a production situation where many different protein products are being purified at the same time, developing a unique wash buffer for each individual protein product requires significant time and resources to screen various buffer components to determine an appropriate wash buffer for each particular protein product. A "generic" intermediate wash buffer that could be used effectively with different types of proteins would be useful and desirable. The present invention provides a method of protein purification using such wash buffer components.

SUMMARY OF THE INVENTION

In one aspect the present invention is directed to a method for purifying a protein comprising an antibody, antibody fragment, or immunoglobulin single variable domain, from a solution containing at least one contaminant by superantigen chromatography comprising: a) adsorbing the protein to the superantigen immobilized on a solid support; b) removing the at least one contaminant by contacting the immobilized superantigen containing the adsorbed protein with a first wash buffer comprising an aliphatic carboxylate; and c) eluting the protein from the superantigen immobilized on the solid support.

In one aspect the present invention is directed to a method for purifying a protein from a contaminated solution thereof by Protein A chromatography comprising:
(a) equilibrating a Protein A immobilized on a solid phase with a Protein A equilibration buffer;
(b) adsorbing the protein from the contaminated solution to the Protein A immobilized on the solid phase;
(c) removing at least one contaminant by washing the solid phase with a first Protein A wash buffer comprising about 50 mM to about 55 mM tris base, about 45 mM to about 50 mM acetic acid, at least one aliphatic carboxylate, at about pH 7.5, wherein the aliphatic carboxylate is selected from the group consisting of about 100 mM to sodium caprylate, about 20 mM sodium decanoate, and about 20 mM sodium dodecanoate; and
(d) recovering the protein from the solid phase with a Protein A elution buffer. In one aspect of the present invention, all of the buffers are made without the addition of NaCl.

In one embodiment the Protein A wash buffer further comprises about 1 mM to about 500 mM sodium acetate. In one embodiment the Protein A wash buffer comprises about 300 mM sodium acetate.

In one aspect the present invention is directed to a method for purifying a protein from a contaminated solution thereof by Protein L chromatography comprising:
(a) equilibrating a Protein L immobilized on a solid phase with a Protein L equilibration buffer;
(b) adsorbing the protein from the contaminated solution to the Protein L immobilized on the solid phase;
(c) removing at least one contaminant by washing the solid phase with a first Protein L wash buffer comprising about 50 mM to about 55 mM tris base, about 45 mM to about 50 mM acetic acid, at least one aliphatic carboxylate, at about pH 7.5, wherein the aliphatic carboxylate is selected from the group consisting of about 100 mM to sodium caprylate, about 20 mM sodium decanoate, and about 20 mM sodium dodecanoate; and
(d) recovering the protein from the solid phase with a Protein L elution buffer. In one aspect of the present invention, all of the buffers are made without the addition of NaCl.

In one embodiment the Protein L wash buffer further comprises about 1 mM to about 500 mM sodium acetate. In one embodiment the Protein L wash buffer comprises about 300 mM sodium acetate.

DETAILED DESCRIPTION OF THE INVENTION

It is to be understood that this invention is not limited to particular methods, reagents, compounds, compositions, or biological systems, which can, of course, vary. It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. Thus, for example, reference to "a polypeptide" includes a combination of two or more polypeptides, and the like.

"About" as used herein when referring to a measurable value such as an amount, a temporal duration, and the like, is meant to encompass variations of ±20% or ±10%, including ±5%, ±1%, and ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Polypeptide," "peptide" and "protein" are used interchangeably herein to refer to a polymer of amino acid residues. A polypeptide can be of natural (tissue-derived) origins, recombinant or natural expression from prokaryotic or eukaryotic cellular preparations, or produced chemically via synthetic methods. The terms apply to amino acid polymers in which one or more amino acid residue is an artificial chemical mimetic of a corresponding naturally occurring amino acid, as well as to naturally occurring amino acid polymers and non-naturally occurring amino acid polymer Amino acid mimetics refers to chemical compounds that have a structure that is different from the general chemical structure of an amino acid, but that functions in a manner similar to a naturally occurring amino acid. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-na-phylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine: D-(trifluoromethyl)-phenylglycine; D-(trifluoromethyl)-phenylalanine: D-p-fluoro-phenylalanine; D- or L-p-biphenylphenylalanine; K- or L-p-methoxy-biphenylphenylalanine: D- or L-2-indole(alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

"Peptide" as used herein includes peptides which are conservative variations of those peptides specifically exemplified herein. "Conservative variation" as used herein denotes the replacement of an amino acid residue by another, biologically similar residue. Examples of conservative variations include, but are not limited to, the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acids, or glutamine for asparagine, and the like. Neutral hydrophilic amino acids which can be substituted for one another include asparagine, glutamine, serine and threonine. "Conservative variation" also includes the use of a substituted amino acid in place of an unsubstituted parent amino acid provided that antibodies raised to the substituted polypeptide also immunoreact with the unsubstituted polypeptide. Such conservative substitutions are within the definition of the classes of the peptides of the invention. "Cationic" as used herein refers to any peptide that possesses a net positive charge at pH 7.4. The biological activity of the peptides can be determined by standard methods known to those of skill in the art and described herein.

"Recombinant" when used with reference to a protein indicates that the protein has been modified by the introduction of a heterologous nucleic acid or protein or the alteration of a native nucleic acid or protein.

As used herein a "therapeutic protein" refers to any protein and/or polypeptide that can be administered to a mammal to elicit a biological or medical response of a tissue, system, animal or human that is being sought, for instance, by a researcher or clinician. A therapeutic protein may elicit more than one biological or medical response. Furthermore, the term "therapeutically effective amount" means any amount which, as compared to a corresponding subject who has not received such amount, results in, but is not limited to, healing, prevention, or amelioration of a disease, disorder, or side effect, or a decrease in the rate of advancement of a disease or disorder. The term also includes within its scope amounts effective to enhance normal physiological function as well as amounts effective to cause a physiological function in a patient which enhances or aids in the therapeutic effect of a second pharmaceutical agent.

All "amino acid" residues identified herein are in the natural L-configuration. In keeping with standard polypeptide nomenclature, abbreviations for amino acid residues are as shown in the following table.

TABLE 1

Amino acid abbreviations.

| 1 Letter | 3 Letter | Amino Acid |
| --- | --- | --- |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | leucine |
| T | Thr | L-threonine |
| V | Val | L-valine |
| P | Pro | L-proline |
| K | Lys | L-lysine |
| H | His | L-histidine |
| Q | Gin | L-glutamine |
| E | Glu | L-glutamic acid |
| W | Trp | L-tryptohan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus.

In another embodiment the polypeptide is an antigen binding polypeptide. In one embodiment the antigen binding polypeptide is selected from the group consisting of a soluble receptor, antibody, antibody fragment, immunoglobulin single variable domain, Fab, F(ab')2, Fv, disulphide linked Fv, scFv, closed conformation multispecific antibody, disulphide-linked scFv, or diabody.

The term "antigen binding polypeptide" as used herein refers to antibodies, antibody fragments and other protein constructs which are capable of binding to an antigen.

The terms Fv, Fc, Fd, Fab, or F(ab)2 are used with their standard meanings (see, e.g., Harlow et al., Antibodies A Laboratory Manual, Cold Spring Harbor Laboratory, (1988)).

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., Proc. Natl. Acad Sci USA, 86:10029-10032 (1989), Hodgson et al., Bio/Technology, 9:421 (1991)). A suitable human acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies—see for example EP-A-0239400 and EP-A-054951.

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

As used herein the term "domain" refers to a folded protein structure which has tertiary structure independent of the rest of the protein. Generally, domains are responsible for discrete functional properties of proteins and in many cases may be added, removed or transferred to other proteins without loss of function of the remainder of the protein and/or of the domain Δn "antibody single variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

The phrase "immunoglobulin single variable domain" refers to an antibody variable domain ($V_H$, $V_{HH}$, $V_L$) that specifically binds an antigen or epitope independently of a different V region or domain. An immunoglobulin single variable domain can be present in a format (e.g., homo- or hetero-multimer) with other, different variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" which is capable of binding to an antigen as the term is used herein. An immunoglobulin single variable domain may be a human antibody variable domain, but also includes single antibody variable domains from other species such as rodent (for example, as disclosed in WO 00/29004), nurse shark and Camelid $V_{HH}$ dAbs (nanobodies). Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanized according to standard techniques available in the art, and such domains are still considered to be "domain antibodies" according to the invention. As used herein "$V_H$ includes camelid $V_{HH}$ domains. NARV are another type of immunoglobulin single variable domain which were identified in cartilaginous fish including the nurse shark. These domains are also known as Novel Antigen Receptor variable region (commonly abbreviated to V(NAR) or NARV). For further details see Mol. Immunol. 44, 656-665 (2006) and US20050043519A.

The term "Epitope-binding domain" refers to a domain that specifically binds an antigen or epitope independently of a different V region or domain, this may be a domain antibody (dAb), for example a human, camelid or shark immunoglobulin single variable domain.

As used herein, the term "antigen-binding site" refers to a site on a protein which is capable of specifically binding to antigen, this may be a single domain, for example an epitope-binding domain, or it may be paired $V_H/V_L$ domains as can be found on a standard antibody. In some aspects of the invention single-chain Fv (ScFv) domains can provide antigen-binding sites.

The terms "mAbdAb" and dAbmAb" are used herein to refer to antigen-binding proteins of the present invention. The two terms can be used interchangeably, and are intended to have the same meaning as used herein.

In one aspect the present invention is directed to a method for purifying a protein comprising an antibody, antibody fragment, or immunoglobulin single variable domain, from a solution containing at least one contaminant by superantigen chromatography comprising: a) adsorbing the protein to the superantigen immobilized on a solid support; b) removing the at least one contaminant by contacting the immobilized superantigen containing the adsorbed protein with a first wash buffer comprising an aliphatic carboxylate; and c) eluting the protein from the superantigen immobilized on the solid support.

In one embodiment the affinity chromatography is performed using a superantigen. "Superantigen" refers to generic ligands that interact with members of the immunoglobulin superfamily at a site that is distinct from the target ligand-binding sites of these proteins. Staphylococcal enterotoxins are examples of superantigens which interact with T-cell receptors. Superantigens that bind antibodies include, but are not limited to, Protein G, which binds the IgG constant region (Bjorck and Kronvall, *J. Immunol.*, 133:969 (1984)); Protein A which binds the IgG constant region and $V_H$ domains (Forsgren and Sjoquist, *J. Immunol.*, 97:822 (1966)); and Protein L which binds $V_L$ domains (Bjorck, *J. Immunol.*, 140:1194 (1988). In one embodiment the superantigen is selected from the group consisting of Protein A, Protein G, and Protein L.

When used herein, the term "Protein A" encompasses Protein A recovered from a native source thereof, Protein A produced synthetically (e.g. by peptide synthesis or by recombinant techniques), and variants thereof which retain the ability to bind proteins which have a $C_H2/C_H3$ region. Protein A can be purchased commercially from Repligen, Pharmacia and Fermatech.

As used herein, "affinity chromatography" is a chromatographic method that makes use of the specific, reversible interactions between biomolecules rather than general properties of the biomolecule such as isoelectric point, hydrophobicity, or size, to effect chromatographic separation. "Protein A affinity chromatography" or "Protein A chromatography" refers to a specific affinity chromatographic method that makes use of the affinity of the IgG binding domains of Protein A for the Fc portion of an immunoglobulin molecule. This Fc portion comprises human or animal immunoglobulin constant domains $C_H2$ and $C_H3$ or immunoglobulin domains substantially similar to these. Protein A encompasses native protein from the cell wall of *Staphylococcus aureas*, Protein A produced by recombinant or synthetic methods, and variants that retain the ability to bind to an Fc region. In practice, Protein A chromatography involves using Protein A immobilized to a solid support. See Gagnon, Protein A Affinity Chromotography, Purification Tools for Monoclonal Antibodies, pp. 155-198, Validated Biosystems, 1996. Protein G and Protein L may also be used for affinity chromatography. The solid support is a non-aqueous matrix onto which Protein A adheres (for example, a column, resin, matrix, bead, gel, etc). Such supports include agarose, sepharose, glass, silica, polystyrene, collodion charcoal, sand, polymethacrylate, cross-linked poly (styrene-divinylbenzene), and agarose with dextran surface extender and any other suitable material. Such materials are well known in the art. Any suitable method can be used to affix the superantigen to the solid support. Methods for affixing proteins to suitable solid supports are well known in the art. See e.g. Ostrove, in Guide to Protein Purification, Methods in Enzymology, 182: 357-371, 1990. Such solid supports, with and without immobilized Protein A or Protein L, are readily available from many commercial sources including such as Vector Laboratory (Burlingame, Calif.), Santa Cruz Biotechnology (Santa Cruz, Calif.), BioRad (Hercules, Calif.), Amersham Biosciences (part of GE Healthcare, Uppsala, Sweden) and Millipore (Billerica, Mass.).

The aliphatic carboxylate can be either straight chained or branched. In certain embodiments the aliphatic carboxylate is an aliphatic carboxylic acid or salt thereof, or the source of the aliphatic carboxylate is an aliphatic carboxylic acid or salt thereof. In certain embodiments, the aliphatic carboxylate is straight chained and selected from the group consisting of methanoic (formic) acid, ethanoic (acetic) acid, propanoic (propionic) acid, butanoic (butyric) acid, pentanoic (valeric) acid, hexanoic (caproic) acid, heptanoic (enanthic) acid, octanoic (caprylic) acid, nonanoic (pelargonic) acid, decanoic (capric) acid, undecanoic (undecylic) acid, dodecanoic (lauric) acid, tridecanoic (tridecylic) acid, tetradecanoic (myristic) acid, pentadecanoic acid, hexadecanoic (palmitic) acid, heptadecanoic (margaric) acid, octadecanoic (stearic) acid, and icosanoic (arachidic) acid or any salts thereof. Accordingly, the aliphatic carboxylate can comprise a carbon backbone of 1-20 carbons in length. In one embodiment the aliphatic carboxylate comprises a 6-12 carbon backbone. In one embodiment the aliphatic carboxylate is selected from the group consisting of caproate, heptanoate, caprylate, decanoate, and dodecanoate. In one embodiment the source of the aliphatic carboxylate is selected from the group consisting of an aliphatic carboxylic acid, a sodium salt of an aliphatic carboxylic acid, and a potassium salt of an aliphatic carboxylic acid. In one embodiment the wash buffer comprises sodium caprylate, sodium decanoate, or sodium dodecanoate.

In one embodiment the wash buffer comprises about 10 mM to about 125 mM sodium caprylate, about 1 mM to about 30 mM sodium decanoate, or about 1 mM to about 30 mM sodium dodecanoate. In one embodiment the wash buffer comprises about 100 mM sodium caprylate, about 20 mM sodium decanoate, or about 20 mM sodium dodecanoate. In one embodiment the wash buffer comprises about 1 mM to about 500 mM sodium acetate. In one embodiment the wash buffer comprises about 300 mM sodium acetate.

In one embodiment the at least one contaminant is a host cell protein or host cell DNA. In certain embodiments the host cell is selected from the group consisting of selected from the group consisting of CHO cells, NS0 cells, Sp2/0 cells, COS cells, K562 cells, BHK cells, PER.C6 cells, and HEK cells. The host cell may be a bacterial cell selected from the group consisting of *E. coli* (for example, W3110, BL21), *B. subtilis* and/or other suitable bacteria; eukaryotic cells, such as fungal or yeast cells (e.g., *Pichia pastoris, Aspergillus* sp., *Saccharomyces cerevisiae, Schizosaccharomyces pombe, Neurospora crassa*).

A "buffer" is a buffered solution that resists changes in pH by the action of its acid-base conjugate components.

An "equilibration buffer" herein is that used to prepare the solid phase for chromatography.

The "loading buffer" is that which is used to load the mixture of the protein and contaminant(s) onto the chromatography matrix. The equilibration and loading buffers can be the same.

The "elution buffer" is used to elute proteins from the chromatography matrix.

A "salt" is a compound formed by the interaction of an acid and a base.

In one embodiment the wash buffer comprises an organic acid, an alkaline metal or ammonium salt of the conjugate base of the organic acid, and an organic base. In one embodiment the wash buffer is made without the addition of NaCl.

In one embodiment, the organic acid includes, but is not limited to, formic acid, acetic acid, lactic acid, citric acid, malic acid, maleic acid, glycine, phosphoric acid, glycylclycine, succinic acid, TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

In one embodiment, the organic base includes, but is not limited to, the group consisting of tris base, arginine, Bistris, Bis-tris-Propane, Bicine (N,N-bis(2-hydroxyethyl)glycine), HEPES (4-2-hydroxyethyl-1-piperazineethanesulfonic acid), TAPS (3-{[tris(hydroxymethyl)methyl]amino}propanesulfonic acid), and Tricine (N-tris(hydroxymethyl)methylglycine).

In one embodiment, the conjugate base of the organic acid is the sodium, potassium, or ammonium salt of the conjugate base of the organic acid. In one embodiment, the organic acid is acetic acid and the conjugate base of acetic acid is the sodium salt.

In one embodiment, the protein is an antigen binding protein. In one embodiment, the antigen binding protein is an antibody. In one embodiment the antibody is of the IgG class. In one embodiment, the antigen binding protein is a immunoglobulin single variable domain.

In one aspect the present invention is directed to a method for purifying a protein from a contaminated solution thereof by Protein A chromatography comprising:
  (a) equilibrating a Protein A immobilized on a solid phase with a Protein A equilibration buffer;
  (b) adsorbing the protein from the contaminated solution to the Protein A immobilized on the solid phase;
  (c) removing at least one contaminant by washing the solid phase with a first Protein A wash buffer comprising about 50 mM to about 55 mM tris base, about 45 mM to about 50 mM acetic acid, at least one aliphatic carboxylate, at about pH 7.5, wherein the aliphatic carboxylate is selected from the group consisting of about 100 mM to sodium caprylate, about 20 mM sodium decanoate, and about 20 mM sodium dodecanoate; and
  (d) recovering the protein from the solid phase with a Protein A elution buffer. In one embodiment, all of the buffers are made without the addition of NaCl. In one embodiment the Protein A wash buffer further comprises about 1 mM to about 500 mM sodium acetate. In one embodiment the Protein A wash buffer comprises about 300 mM sodium acetate.

In one embodiment the equilibration buffer comprises about 50 mM to about 55 mM tris base, about 45 mM to about 50 mM acetic acid, at about pH 7.2; and the elution buffer comprises 1.8 mM sodium acetate and about 28.2 mM to about 300 mM acetic acid, at about pH 2.4 to about pH 3.6.

In one embodiment the method further comprises the following step after step (c) and before step (d): removing contaminants by washing the solid phase with a second Protein A wash buffer comprising 55 mM tris base, 45 mM acetic acid, at about pH 7.2. In one embodiment, the second Protein A wash buffer is made without the addition of NaCl.

In one embodiment the method further comprises the following steps after step (d): (e) titrating the solution containing the recovered protein to about pH 3.0 with 30 mM acetic acid, 100 mM HCl; (f) allowing the solution of step (e) to remain at about pH 3.0 for about 30 to about 60 minutes; and (g) adjusting the pH of the solution of step (f) to about pH 7.5 with 1 M tris.

In one embodiment the method further comprises filtering the solution produced by step (g).

In one aspect the present invention is directed to a method for purifying a protein from a contaminated solution thereof by Protein L chromatography comprising:
  (a) equilibrating a Protein L immobilized on a solid phase with a Protein L equilibration buffer;
  (b) adsorbing the protein from the contaminated solution to the Protein L immobilized on the solid phase;
  (c) removing at least one contaminant by washing the solid phase with a first Protein L wash buffer comprising about 50 mM to about 55 mM tris base, about 45 mM to about 50 mM acetic acid, at least one aliphatic carboxylate, at about pH 7.5, wherein the aliphatic carboxylate is selected from the group consisting of about 100 mM to sodium caprylate, about 20 mM sodium decanoate, and about 20 mM sodium dodecanoate; and
  (d) recovering the protein from the solid phase with a Protein L elution buffer. In one embodiment, all of the buffers are made without the addition of NaCl. In one embodiment the Protein L wash buffer further comprises about 1 mM to about 500 mM sodium acetate. In one embodiment the Protein L wash buffer comprises about 300 mM sodium acetate.

In one embodiment the equilibration buffer comprises about 50 mM to about 55 mM tris base, about 45 mM to about 50 mM acetic acid, at about pH 7.2; and the elution buffer comprises 1.8 mM sodium acetate and about 28.2 mM to about 300 mM acetic acid, at about pH 2.4 to about pH 3.6.

In one embodiment the method further comprises the following step after step (c) and before step (d): removing contaminants by washing the solid phase with a second Protein L wash buffer comprising 55 mM tris base, 45 mM acetic acid, at about pH 7.2. In one embodiment, the second Protein L wash buffer is made without the addition of NaCl.

In one embodiment the method further comprises the following steps after step (d): (e) titrating the solution containing the recovered protein to about pH 3.0 with 30 mM acetic acid, 100 mM HCl; (f) allowing the solution of step (e) to remain at about pH 3.0 for about 30 to about 60 minutes; and (g) adjusting the pH of the solution of step (f) to about pH 7.5 with 1 M tris.

In one embodiment the method further comprises the filtering the solution produced by step (g).

The "solution" may be a cell culture medium, for example a cell culture feedstream. The feedstream may be filtered. The solution may be a Clarified Unprocessed Broth (CUB) (or clarified fermentation broth/supernatant). The CUB is also known as a cell culture supernatant with any cells and/or cellular debris removed by clarification. Alternatively, at least one periplasmic extract is harvested using methods known in the art. The solution may be a lysed preparation of cells expressing the protein (eg solution is a lysate).

"Contaminant" refers to any foreign or undesirable molecule that is present in the load sample prior to superantigen chromatography or following superantigen chromatography in the eluate. There may be "process impurities" present.

These are impurities that are present as a result of the process in which the protein of interest is produced. For example, these include host cell proteins (HCP), RNA, and DNA (for example viruses). "HCP" refers to proteins, not related to the protein of interest, produced by the host cell during cell culture or fermentation, including intracellular and/or secreted proteins. An example of a host cell protein is a protease, which can cause damage to the protein of interest if still present during and after purification. For example, if a protease remains in the sample comprising the protein of interest, it can create product-related substances or impurities which were not originally present. The presence of proteases can cause decay of the protein of interest over time during the purification process, and/or in the final formulation. Removal of HCP, or reduced levels of HCP, by definition equals removal or reduction of proteases.

Process impurities also include components used to grow the cells or to ensure expression of the protein of interest, for example, solvents (eg methanol used to culture yeast cells), antibiotics, methotrexate (MTX), media components, flocculants, etc. Also included are molecules that are part of the superantigen solid phase that leach into the sample during prior steps, for example, Protein A, Protein G, or Protein L. Contaminants also include "product-related substances" which include proteins that retain their activity but are different in their structure; and "product-related impurities" which include proteins that have lost their activity because of their difference in structure. These product-related variants include, for example, high molecular weight species (HMWs), low molecular weight species (LMWs), aggregated proteins, prescursors, degraded proteins, misfolded proteins, underdisulfide-bonded proteins, fragments, and deamidated species.

The presence of any one of these impurities in the eluate can be measured to establish whether the wash step has been successful. For example, we have shown a reduction in the level of HCP detected measured by ng HCP per mg of protein (see the Examples).

Accordingly, the eluate from the superantigen solid support may contain the protein in a sample with HCP or DNA present in about 5000 parts per million (ppm) or less, 4000 parts per million (ppm) or less, 3000 parts per million (ppm) or less, 2,500 parts per million (ppm) or less, 2000 parts per million (ppm) or less, 1500 parts per million (ppm) or less, 1000 parts per million (ppm) or less, about 900 parts per million (ppm) or less, about 800 parts per million (ppm) or less, about 700 parts per million (ppm) or less, about 600 parts per million (ppm) or less, about 500 parts per million (ppm) or less, about 400 parts per million (ppm) or less, about 300 parts per million (ppm) or less, about 200 parts per million (ppm) or less, about 100 parts per million (ppm) or less, about 90 ppm or less, about 80 ppm or less, about 70 ppm or less, about 60 ppm or less, or about 50 ppm or less. "Ppm" is equivalent to ng/mg and "ppb" ("parts per billion") is equivalent to pg/mg.

A reduction may be shown when compared to a control wash step without an aliphatic carboxylate. Alternatively, the reduction may be shown when compared to a control wash step without an aliphatic carboxylate and sodium acetate.

A method as described, wherein the recovery of the protein of interest from the eluate is 100%, 99%, 98%, 97%, 96%, 95%, 90%, 85%, 80%, 70%, 60%, 50% or less, including any discrete value within the range of 100% to 50% or any subrange defined by any pair of discrete values within this range, following the wash step of the invention. Percent (%) recovery in the eluate is calculated by determining the amount of protein of interest in the eluate as a percentage of the amount of protein of interest applied to the column according to the following formula:

$$\text{Percentage Recovery} = \text{Amount of product in the eluate} \times 100$$

Amount of Product in the Load

The amount of contaminant present in the eluate may be determined by ELISA, OCTET, or other methods to determine the level or one or more of the contaminants described above. In the Examples described herein, an ELISA method is used to determine the level of HCP in a sample.

Example 1—Materials and Methods

All chromatographic processes were carried out using an AKTA Explorer 100 system from GE Healthcare (Uppsala, Sweden). Concentration of pure protein samples was determined by measuring absorbance at 280 nm using a Thermo Scientific NanoDrop 1000 (RN). Protein concentrations from crude samples were determined using a POROS Protein A column (2.1×30 mm) obtained from Applied Biosystems (Foster City, CA) on an Agilent 1100 HPLC from Hewlett Packard (Palo Alto, CA). MabSelect SuRe Protein A media was obtained from GE Healthcare (Uppsala, Sweden). Vantage columns were obtained from Millipore Corporation (Bedford, MA). Turbidity measurements were taken using a 2100P Tubidimeter with glass sample cells catalog #24347-06 obtained from HACH Company (Loveland, CO, USA). All chemicals were obtained from JT Baker (Phillipsburg, NJ) or Sigma Aldrich (St Louis, MO) and were of USP grade.

All chromatography experiments were carried out with a 1.1×25 cm MabSelect SuRe column on an AKTA Explorer 100 chromatography system unless otherwise noted. The antibody concentration of cell culture filtrate was determined by analytical protein A or was carried out by the Biacore protein concentration assay by the Bioanalytical Sciences group at GSK, Upper Merion.

Example 2—Initial Screening of Wash Buffer Additives

Figure 1:
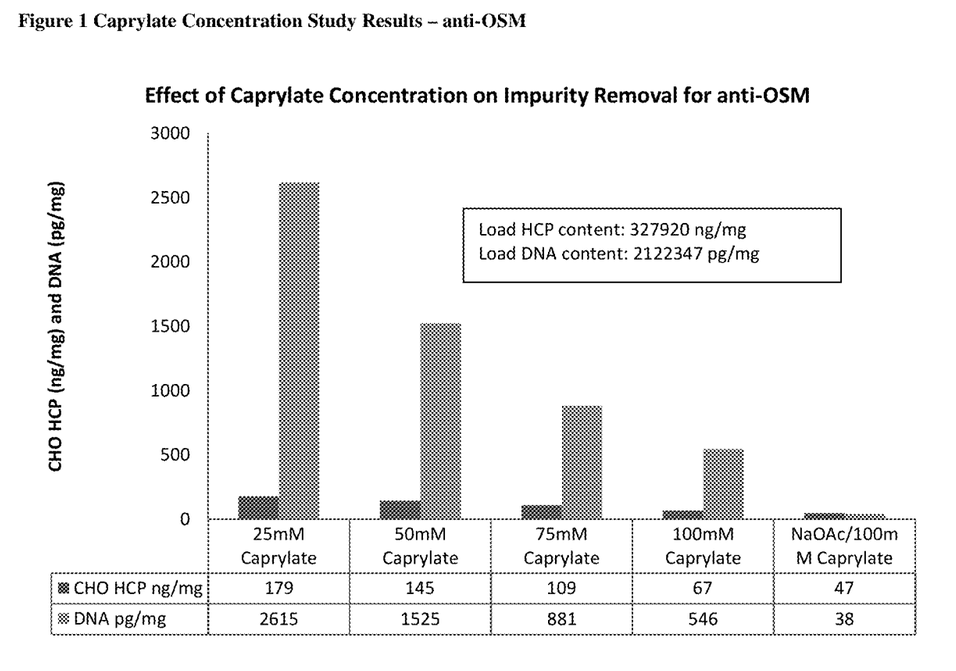
FIG. 1. Caprylate Concentration Study Results—anti-OSM.

Buffers were prepared by titrating to specific pHs using acetic acid or tris base. As a control, screening conditions were compared to results from a wash buffer similar to a standard high-salt protein A wash buffer, 50 mM tris, acetic acid, 1 M NaCl, pH 7.2. Refer to FIG. 1 for a complete list of the five experimental conditions tested and Tables 3 and 4 for the corresponding results. The wash buffers were tested in protein A chromatography of GSK assets anti-OSM (GSK315234) and anti-IL13 (GSK679586) cell culture filtrate. These two separate cases resulted in similar HCP and DNA reduction trends. Impurity levels in Protein A products for the Triton X100 and Triton X114 wash buffers were not evaluated further due to an altered and atypical elution profile and excessive product loss. The PS80 containing buffer, a non-ionic ethylene oxide polymer based surfactant, showed marginal clearance compared to the standard 1M NaCl wash buffer. The greatest reduction in HCP and DNA came from the wash buffer containing 100 mM sodium caprylate, a sodium salt of the carboxylic acid, octanoic acid. The 100 mM Caprylate buffer resulted in approximately a 5 fold reduction in HCP compared to the control for both anti-OSM and anti-IL13. Furthermore, it resulted in a 100 fold and 60 fold reduction in DNA compared to the control for anti-IL13 and anti-OSM respectively. Refer to Table 3 and Table for complete yield, HCP, DNA, and SEC data for anti-OSM and anti-IL13 with wash screening conditions.

TABLE 2

Experimental Summary of Wash Conditions

| CV | Flow Rate (cm/hr) | Buffer |
|---|---|---|
| 3.5 CV | 400 | Equil - 50 mM tris, acetic acid, 1M NaCl, pH 7.2 |
| 35 mg/mL | 300 | Load at 300 cm/hr |
| 5 CV | 400 | Wash 1 - Run # |
| | | 1 - 50 mM tris, acetic acid, 1M NaCl, pH 7.2 |
| | | 2 - 50 mM tris, acetic acid, 1M NaCl, 1% PS80, pH 7.2 |
| | | 3 - 50 mM tris, acetic acid, 1M NaCl, 1% Triton X100, pH 7.2 |
| | | 4 - 50 mM tris, acetic acid, 1M NaCl, 1% Triton X114, pH 7.2 |
| | | 5 - 50 mM tris, acetic acid, 1M NaCl, 100 mM Sodium Caprylate, pH 7.2 |
| 5 CV | 400 | Wash 2 - 50 mM tris, acetic acid, pH 7.2 |
| 4 CV | 400 | Elution - 30 mM acetic acid, tris base, pH 3.6 |
| 3 CV | 400 | Strip - pH 1.5 HCl |
| 3 CV | 300 | Clean - 0.1N NaOH |
| 4 CV* | 300 | Store - 20% Ethanol, 50 mM Phosphate, pH 7.0 |

*Only run on last cycle to store column

Example 3—Effect of Caprylate Concentration on Impurity Clearance

Figure 2:
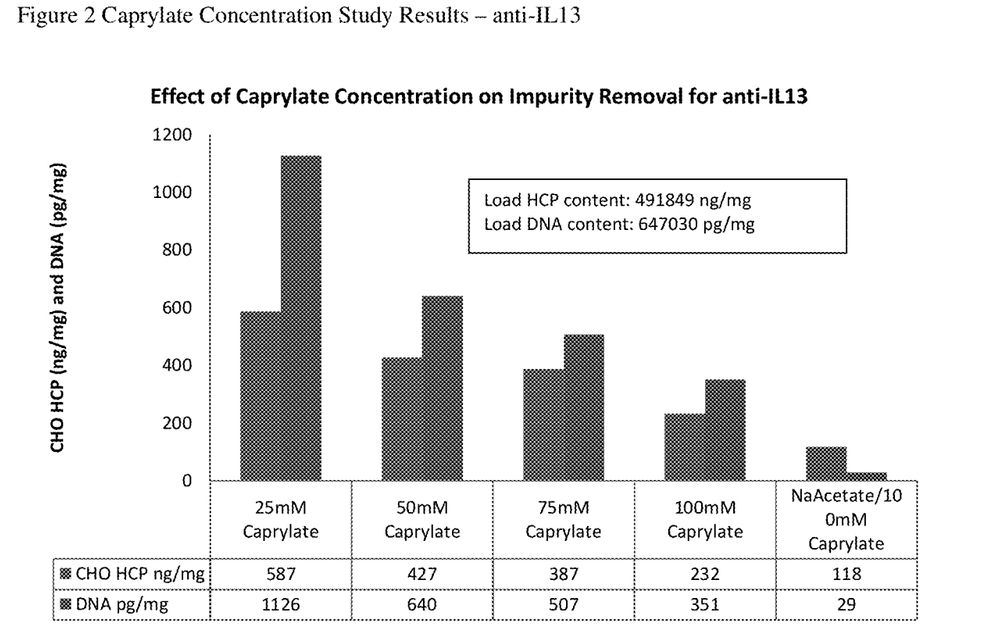
FIG. 2. Caprylate Concentration Study Results—anti-IL13.

To examine the effects of sodium caprylate concentration on removal of impurities, a series of sodium caprylate concentrations were tested. Refer to Table 5 for a list of buffers and flow rates used to examine the concentration effects of caprylate on the removal of impurities for anti-OSM and anti-IL13. The data from the caprylate concentration studies are summarized in FIG. 1 and FIG. 2 for anti-OSM and anti-IL13. For both anti-IL13 and anti-OSM chromatography, changes in caprylate concentration clearly impact the reduction of CHO HCP and DNA. The higher the concentration of caprylate the greater the reduction of HCP and DNA for both anti-OSM and anti-IL13 was observed. However, the greatest reduction in HCP and DNA was observed with a combination of sodium caprylate and 0.3 M sodium acetate. The combined effect of the detergent and a salt increased the clearance capacity of the buffer compared to a detergent or a salt alone.

The maximum sodium caprylate concentration tested in this study was 100 mM sodium caprylate due to an empirically determined solubility of approximately 125 mM sodium caprylate at a pH of 7.2. Since solubility is expected to increase at higher pH, higher concentrations of caprylate could be tested by adjusting the buffer system and components, if greater host cell contaminant removal were required. Based on this work, however, we determined that

TABLE 3

Experimental Results of anti-IL13 Wash Development

| Wash Buffer | Sample | HCP (ng/mg) | DNA (pg/mg) | % Monomer SEC | % Yield Biacore | Fold reduction relative to control | |
|---|---|---|---|---|---|---|---|
| | | | | | | HCP | DNA |
| | Load | 458282 | 3219895 | — | — | | |
| 50 mM Tris, Acetic Acid, 1M NaCl, pH 7.2 (control) | Salt wash- MabSelect SuRe Pool | 648 | 537 | 96.8% | 81.1% | 1 | 1 |
| 50 mM Tris, Acetic Acid, 1M NaCl, 100 mM Sodium Caprylate, pH 7.2 | Caprylate wash- MabSelect SuRe Pool | 140 | 5 | 97.0% | 79.2% | 4.6 | 107 |
| 50 mM Tris, Acetic Acid, 1M NaCl, 1% PS80, pH 7.2 | PS80 wash- MabSelect SuRe Pool | 607 | 253 | 96.9% | 77.2% | 1.1 | 2.1 |

TABLE 4

Experimental Results of anti-OSM Wash Development

| Wash Buffer | Sample | HCP (ng/mg) | DNA (pg/mg) | % Monomer SEC | % Yield Biacore |
|---|---|---|---|---|---|
| | Load | 242258 | 13550 | — | — |
| 50 mM Tris, Acetic Acid, 1M NaCl, pH 7.2 | Salt wash - MabSelect SuRe Pool | 136 | 59 | 99.3% | 95.1% |
| 50 mM Tris, Acetic Acid, 1M NaCl, 100 mM Sodium Caprylate, pH 7.2 | Caprylate wash - MabSelect SuRe Pool | 23 | 1 | 98.9% | 95.3% |
| 50 mM Tris, Acetic Acid, 1M NaCl, 1% PS80, pH 7.2 | PS80 wash - MabSelect SuRe Pool | 135 | 49 | 98.8% | 99.3% |

100 mM sodium caprylate in combination with 0.3 M sodium acetate gave adequate removal of host cell impurities.

TABLE 5

Effect of Caprylate Concentration Experimental Design

| CV | Flow Rate (cm/hr) | Buffer |
|---|---|---|
| 3.5 CV | 400 | Equil - 50 mM tris, acetic acid, pH 7.2 |
| 35 mg/mL | 300 | Load at 300 cm/hr |
| 5 CV | 400 | Wash 1 - Run # |
| | | 1 - 50 mM tris, acetic acid, 25 mM Sodium Caprylate, pH 7.2 |
| | | 2 - 50 mM tris, acetic acid, 50 mM Sodium Caprylate, pH 7.2 |
| | | 3 - 50 mM tris, acetic acid, 75 mM Sodium Caprylate, pH 7.2 |
| | | 4 - 50 mM tris, acetic acid, 100 mM Sodium Caprylate, pH 7.2 |
| | | 5 - 50 mM tris, acetic acid, 0.3M sodium acetate, 100 mM Sodium Caprylate, pH 7.2 |
| 5 CV | 400 | Wash 2 - 50 mM tris, acetic acid, pH 7.2 |
| 4 CV | 400 | Elution - 30 mM acetic acid, tris base, pH 3.6 |
| 3 CV | 400 | Strip - pH 1.5 HCl |
| 3 CV | 300 | Clean - 0.1N NaOH |
| 4 CV* | 300 | Store - 20% Ethanol, 50 mM Phosphate, pH 7.0 |

*Only run on last cycle to store column

Example 4—Carboxylic Acid Screening

Figure 3:
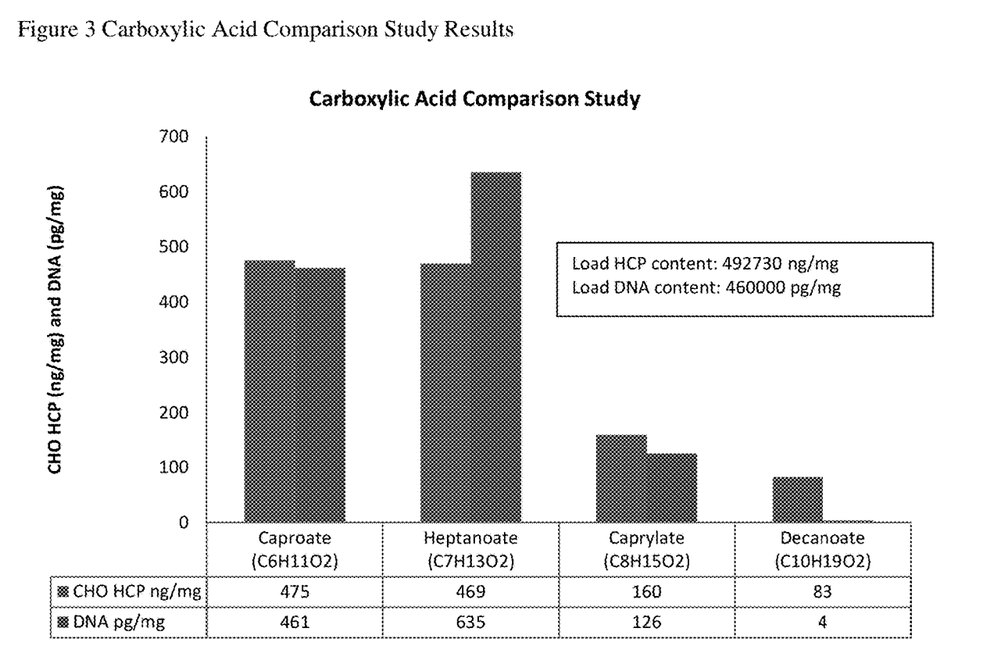
FIG. 3. Carboxylic Acid Comparison Study Results.

Sodium caprylate is the sodium salt of caprylic acid, consisting of an eight carbon long aliphatic chain belonging to a class of carboxylic acids. These amphipathic saturated unbranched salts act as a detergent due to their saturated carbon tails and charged carboxyl head group. To determine the effect of the carbon tail length on contaminant removal several other sodium salts were tested. These other salts tested include sodium caproate, sodium heptanoate, sodium caprylate, sodium decanoate, and sodium dodecanoate. The experimental design is summarized in Table 6. The results of this experiment are summarized in FIG. 3. Sodium dodecanoate was excluded from the analysis due to the low yield and altered elution behaviour observed in preliminary experiments. Though all the different salts resulted in similar product yields, with the exception of dodecanoate, each resulted in very different impurity profiles. As the carbon number in the chain increased impurity levels decreased. The sodium salts with carbon chains less than sodium caprylate (C8) resulted in much higher impurity levels. The best two candidates for a wash buffer additive are sodium caprylate and sodium decanoate.

TABLE 6

Experimental Design - Carboxylic Acid Comparison

| CV | Flow Rate (cm/hr) | Buffer |
|---|---|---|
| 3.5 CV | 400 | Equil - 50 mM tris, acetic acid, pH 7.2 |
| 35 mg/mL | 300 | Load at 300 cm/hr |
| 5 CV | 400 | Wash 1 - Run # |
| | | 1 - 55 mM tris, acetic acid, 0.3M sodium acetate, 100 mM Sodium caproate, pH 7.5 |
| | | 2 - 55 mM tris, acetic acid, 0.3M sodium acetate, 100 mM Sodium heptanoate, pH 7.5 |
| | | 3 - 55 mM tris, acetic acid, 0.3M sodium acetate, 100 mM Sodium Caprylate, pH 7.5 |
| | | 4 - 55 mM tris, acetic acid, 0.3M sodium acetate, 20 mM Sodium decanoate, pH 8.0 |
| | | 5 - 55 mM tris, acetic acid, 0.3M sodium acetate, 20 mM Sodium dodecanoate, pH 8.0 |
| 5 CV | 400 | Wash 2 - 50 mM tris, acetic acid, pH 7.2 |
| 4 CV | 400 | Elution - 30 mM acetic acid, tris base, pH 3.6 |
| 3 CV | 400 | Strip - pH 1.5 HCl |
| 3 CV | 300 | Clean - 0.1N NaOH |
| 4 CV* | 300 | Store - 20% Ethanol, 50 mM Phosphate, pH 7.0 |

*Only run on last cycle to store column

Example 5—Effect of Optimized Wash on Turbidity

The effects of the optimized caprylate wash on downstream unit operations were also explored; with special focus on its impact on minimizing post-protein A precipitation and enhancing filterability. Anti-IL13 cell culture filtrate from anti-IL13 cell culture filtrate at 1.16 g/L was processed over a 2.6×27 cm MabSelect SuRe column using two different wash regimes. Half of this material was processed through protein A chromatography using the optimized wash regime incorporating sodium caprylate. The other half of the material was processed with equilibration buffer in place of the caprylate wash. Using turbidity as a determinate of filterability, turbidity measurements of the eluate pools were recorded. The eluates were then titrated to pH 3.5 with 30 mM acetic acid, 100 mM hydrochloric acid. The turbidity measurements were again measured and recorded. Following a one hour incubation of the eluate samples at pH 3.5 they were then titrated to pH 6.0 in preparation for the next unit operation. Turbidity measurements of the pH adjusted pools were measured and recorded. The resulting data is summarized in Table and the impurity profile is presented in Table. Considering turbidity as an indicator of filterability, the caprylate wash would reduce some of the burden on filtration due to a 50% decrease in turbidity of the anion exchange load material.

TABLE 7 anti-IL13 Turbidity Measurements

| Turbidity | With Caprylate NTU | Without Caprylate NTU |
|---|---|---|
| MabSure Pool | 36 | 79 |
| Low pH Pool | 10 | 10 |
| pH 6.0 Adjusted Pool | 64 | 134 |

TABLE 8

Effect of Caprylate Wash on Purity of Post-
Protein A anti-IL13 Impurity Profiles

|  | With Caprylate | | Without Caprylate | |
|---|---|---|---|---|
| Sample | HCP ng/mg | DNA pg/mg | HCP ng/mg | DNA pg/mg |
| MabSure Pool | 12 | 7 | 244 | 222 |
| Low pH Pool | 15 | 7 | 248 | 134 |
| pH 6.0 Adjusted Pool | 6 | <10 | 195 | <10 |

Example 6—Domain Antibody Purification Using Protein a Caprylate Buffer in Tris-Acetate Buffer DOM0100, a 25 kDa ($V_k$-$V_H$ albudAb+TNFR1dAb) dAb molecule expressed in *E. coli* was purified using protein A, MabSelect Xtra from GE Healthcare packed in a 0.5×20 cm column. The flow rate was 300 cm/hr for all the steps. After equilibration with 55 mM tris-base, 45 mM acetic acid, pH7.5, cell culture filtrate was loaded on the column at 13.5 mg/mL of resin. The load titer was 1.88 mg/mL. The column was then washed using 5 column volumes of 55 mM tris-base, 45 mM acetic acid, 300 mM sodium acetate, 100 mM sodium caprylate, pH7.5. The protein was then eluted and thereafter the column was cleaned, sanitized and stored. The analysis of the elution peak gave 1,440 ppm HCPs (host cell proteins) by ELISA for a 74.9% yield. The same experiment repeated twice under the same conditions but with a high salt wash instead of the caprylate wash gave 2,398 ppm and 2,456 ppm HCPs by ELISA for a yield of 77.2% and 76.0% respectively. The effect of the chromatographic sequence evaluated in a 0.5 cm×10 cm column matching the residence time had no effect on the dynamic binding capacity up to 150 cycles. Resin selectivity was equally investigated for MabSelect and base stable MabSelect SuRe using the same chromatographic sequence and gave comparable HCP product quality.

Example 7—Purification of DAT06 dAb Using Protein L, Caprylate Wash and Tris-Acetate Buffer DAT06, a 11.5 kDa ($V_k$) dAb molecule expressed in *E. coli* was purified using protein L (Capto L from GE Healthcare) packed in a 0.5 cm×20 cm column. The flow rate was 300 cm/hr for all the steps. After equilibration with 52 mM tris-base, 48 mM acetic acid, pH7, cell culture filtrate was loaded at 13 mg/mL of resin. The column was then washed using SCV, 52 mM tris-base, 48 mM acetic acid, 100 mM sodium caprylate, pH7, before to be re-equilibrated, eluted, cleaned, sanitized and stored. The analysis of the elution peak gives 5,815 ppm HCPs by ELISA for a recovery of 96.4%. In comparison, the same chromatographic sequence with a 52 mM tris, 48 mM acetic acid, 2M NaCl, pH7.0 high salt wash step gives 7,476 ppm HCPs by ELISA and a recovery of 85.1%. A wash step with the equilibration buffer, 52 mM tris, 48 mM acetic acid, pH7.0 gives 12,523 ppm HCPs by ELISA and a recovery of 94.1%.

What is claimed:

1. A method for purifying a protein from a solution by superantigen chromatography comprising:
   a) adsorbing the protein to the superantigen immobilized on a solid support;
   b) removing at least one contaminant by contacting the immobilized superantigen containing the adsorbed protein with a first wash buffer comprising 50 mM to 125 mM sodium caprylate; and
   c) eluting the protein from the superantigen immobilized on the solid support,
   wherein the solution comprises the protein and the at least one contaminant,
   wherein the solution is a cell culture feed stream, and
   wherein the at least one contaminant is selected from the group consisting of a host cell protein and host cell DNA.

2. The method of claim 1, wherein the first wash buffer comprises 50 mM to 100 mM sodium caprylate.

3. The method of claim 1, wherein the first wash buffer comprises 50 mM to 75 mM sodium caprylate.

4. The method of claim 1, wherein the first wash buffer comprises 75 mM to 125 mM sodium caprylate.

5. The method of claim 1, wherein the first wash buffer comprises 75 mM to 100 mM sodium caprylate.

6. The method of claim 1, wherein the superantigen is selected from the group consisting of Protein A, Protein G, and Protein L.

7. The method of claim 1, wherein the wash buffer further comprises 100 mM to 400 mM sodium acetate.

8. The method of claim 1, wherein the protein is selected from the group consisting of soluble receptor, antibody, antibody fragment, immunoglobulin single variable domain, Fab, F(ab')2, Fv, disulfide linked Fv, scFv, closed conformation multispecific antibody, disulphide-linked scFv, and diabody.

9. The method of claim 1, wherein the host cell is selected from the group consisting of *E. coli* cells, CHO cells, NS0 cells, Sp2/0 cells, COS cells, K562 cells, BHK cells, PER.C6 cells, and HEK cells.

10. The method of claim 1, wherein the wash buffer further comprises one selected from the group consisting of an organic acid, an alkaline metal salt of the conjugate base of the organic acid, an ammonium salt of the conjugate base of the organic acid, and an organic base.

11. The method of claim 10, wherein the organic acid is selected from the group consisting of formic acid, acetic acid, lactic acid, citric acid, malic acid, maleic acid, glycine, glycylclycine, succinic acid, TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino) ethanesulfonic acid); and wherein the organic base is selected from the group consisting of tris base, Bis-tris, Bis-tris-Propane, Bicine (N,N-bis(2-hydroxyethyl)glycine), HEPES (4-2-hydroxyethyl-1-piperazineethanesulfonic acid), TAPS (3-{[tris(hydroxymethyl)methyl]amino}propanesulfonic acid), and Tricine (N-tris(hydroxymethyl)methylglycine).

12. The method of claim 10, wherein the conjugate base of the organic acid is one selected from the group consisting of the sodium salt of the conjugate base of the organic acid, the potassium salt of the conjugate base of the organic acid, and the ammonium salt of the conjugate base of the organic acid.

13. A method for purifying a protein from a contaminated solution comprising:
   (a) equilibrating Protein A immobilized on a solid phase with Protein A equilibration buffer or equilibrating Protein L immobilized on a solid phase with Protein L equilibration buffer;
   (b) adsorbing the protein from the contaminated solution to the Protein A or Protein L immobilized on the solid phase;

(c) removing at least one contaminant by washing the solid phase with a first Protein A or a first Protein L wash buffer comprising 50 mM to 55 mM tris base, 45 mM to 50 mM acetic acid, 50 mM to 125 mM sodium caprylate, and (d) recovering the protein from the solid phase with a Protein A elution buffer or a Protein L elution buffer, wherein the contaminated solution comprises the protein and the at least one contaminant, wherein the contaminated solution is a cell culture feed stream, and wherein the at least one contaminant is selected from the group consisting of a host cell protein and host cell DNA.

14. The method of claim 13, further comprising the following step after step (c) and before step (d): removing contaminants by washing the solid phase with a second Protein A wash buffer comprising 55 mM tris base, 45 mM acetic acid, at pH 7.2.

15. The method of claim 13, further comprising the following steps after step (d): (e) titrating the solution containing the recovered protein to pH 3.0 with 30 mM acetic acid, 100 mM HCl; (f) allowing the solution of step (e) to remain at pH 3.0 for about 30 to 60 minutes; and (g) adjusting the pH of the solution of step (f) to pH 7.5 with 1 M tris.

16. The method of claim 13, wherein the Protein A wash buffer or the Protein L wash buffer further comprises 1 mM to about 500 mM sodium acetate.

17. The method of claim 13, wherein the protein is selected from the group consisting of soluble receptor, antibody, antibody fragment, immunoglobulin single variable domain, Fab, F(ab')2, Fv, disulphide linked Fv, scFv, closed conformation multispecific antibody, disulphide-linked scFv, and diabody.

18. The method of claim 1, wherein the protein is expressed by the host cell.

19. The method of claim 13, wherein the protein is expressed by the host cell.

20. The method of claim 15, further comprising filtering the solution produced by step (g).

* * * * *